| United States Patent [19] | [11] | 4,379,941 |
|---|---|---|
| House | [45] | Apr. 12, 1983 |

[54] RESOLUTION OF RACEMIC AMINO ACIDS

[75] Inventor: David W. House, Arlington Heights, Ill.

[73] Assignee: UOP Inc., Des Plaines, Ill.

[21] Appl. No.: 338,199

[22] Filed: Jan. 8, 1982

[51] Int. Cl.$^3$ ............................................. C07B 19/00
[52] U.S. Cl. .................................... 562/401; 548/344; 548/498; 548/535; 560/38; 560/39; 560/43; 562/402
[58] Field of Search ................. 562/401, 402; 560/38, 560/39, 43; 260/326.14 T, 326.85; 548/344

[56] References Cited

U.S. PATENT DOCUMENTS 2,388,688 11/1945 Hass ...................................... 562/401
3,305,591 2/1967 Epstein et al. ....................... 562/401
3,422,135 1/1969 Yamada et al. .................. 562/401 X

OTHER PUBLICATIONS

"Advances in Chromatography," 16 176–183, (1978).

Halpern and Westley, *Chem. Comm.*, 421, (1965).
Harada and Hayakawa, *Bull. Chem. Soc. Japan*, 37, 191 (1964).

*Primary Examiner*—Natalie Trousof
*Assistant Examiner*—Vera C. Clarke
*Attorney, Agent, or Firm*—James R. Hoatson, Jr.; Eugene I. Snyder; William H. Page, II

[57] ABSTRACT

Racemic amino acids can be readily resolved by conversion to their diastereomeric esters of an optically active 2-isopropyl-5-methylcyclohexanol and separating the diastereomers by chromatography. It has been observed that the separation of the diastereomeric esters is relatively insensitive to the support or the solvent used as eluant. Thus, satisfactory separation occurs under a broad variety of conditions. The optically active amino acid can be obtained by base catalyzed hydrolysis of the purified diastereomer with high optical purity.

6 Claims, No Drawings

RESOLUTION OF RACEMIC AMINO ACIDS

Living systems long have been recognized as being extremely stereoselective and represent perhaps the most prevalent chiral environment. A result of the chirality is that as a general rule living systems utilize only one enantiomer of those metabolites which possess chiral centers. The essential amino acids are one such example, where only those of the L configuration are utilized by man. Another example is the amino acid 3,4-dihydroxyphenylalanine, where the L enantiomer is the only one pharmacologically active in the treatment of Parkinson's disease.

The challenge is either to prepare optically active amino acids directly by a synthetic scheme utilizing a chiral environment, or to efficiently obtain optically active amino acids from their racemates. Although substantial progress has been made in syntheses in a chiral environment, for example, use of chiral reagents, nonetheless the more usual way of preparing optically active material from inactive precursors is by separation from a recemic mixture of one or both of its components, i.e., the classical method of optical resolution.

One method of optical resolution utilizes the different physical properties of diastereomers to purify at least one diastereomer by conventional separation methods. The desired enantiomer is then obtained from the purified diastereomer by an appropriate chemical conversion. Fractional crystallization commonly is employed as the method of separating diastereomers. A resolution of amino acids could be based on the work of Harada and Hayakawa, *Bull Chem. Soc. Japan*, 37, 191 (1964), who fractionated the diastereomeric hydrochloride salts of the menthyl esters of amino acids by seeding a supersaturated solution with one diastereomer. Another approach could be patterned after Halpern and Westley, *Chem. Comm.*, 421 (1965), who observed that the diastereomeric para-toluenesulfonate salts of menthyl esters of amino acids could be readily fractionally crystallized.

chromatographic separation of diastereomers by an achiral stationary phase represents an alternative to their separation by crystallization, as described in, for example, "Advances in Chromatography" Vol. 16, pp. 177–83 (1978). For a chromatographic separation of diastereomers to be commercially successful as a method of resolving amino acids, stringent requirements are placed on the diastereomers. One requirement is that optically active amino acids must be regenerable in high chemical and optical yield. Another requirement is that the diastereomers be readily separable on a wide variety of stationary phases and using a diversity of eluants, so that the method itself is relatively insensitive to changes in supply and quality of materials, and is relatively undemanding in process control. A basic observation which acts as a foundation for this invention is that diastereomeric esters of certain optically active cyclohexanols and recemic amino acids are readily separable under a broad diversity of chromatographic conditions. Since the optically active enantiomers of the amino acid are readily regenerable from the separate diastereomers by various means in high chemical and stereochemical yield and purity, the aforementioned observation provides the basis for a particularly successful method of resolving amino acids. Additionally, the optically active cyclohexanol used as the resolving agent also can be recovered in high yield to be reused in other cycles of diastereomer preparation, separation, and enantiomeric amino acid regeneration.

SUMMARY OF THE INVENTION

An object of this invention is to obtain optically active amino acids from their racemates. An embodiment is a process comprising the chromatographic separation of esters of racemic amino acids with optically active cyclohexanols, hydrolyzing the purified diastereomers, and recovering the optically active amino acids regenerated thereby. In a more specific embodiment, the cyclohexanol is a 2-isopropyl-5-methylcyclohexanol. In a still more specific embodiment the cyclohexanol is menthol.

DESCRIPTION OF THE INVENTION

The invention described herein is a method of preparing optically active amino acids comprising contacting a solution of the diastereomeric esters from a racemic amino acid and an optically active cyclohexanol with a chromatographic support, eluting the support with a solvent under chromatographic conditions, collecting at least one effluent fraction containing a purified diastereomer, treating the purified diastereomer to liberate the optically active amino acid, and recovering the amino acid. This invention is made possible by the observation that the diastereomeric esters of 2-isopropyl-5-methylcyclohexanol and amino acids are easily separated on a variety of chromotographic supports with a diversity of solvents as eluants.

Diastereomers are compounds with at least two chiral centers, at least one of which is different and at least one of which is the same. In the case where the diastereomers contain two chiral centers, there are two sets of diastereomers, each set being composed of two enantiomers. The members of each diastereomeric set differ in that one chiral center is the same and the other center is different. For example, where A represents an amino acid, M represents menthol, and the notations d and l represent rotations of polarized light, the diastereomeric sets of the esters of menthol with amino acids are, (1) *l-M-d-A*    (3) *l-M-l-A*
(2) *d-M-l-A*    (4) *d-M-d-A* where (1) and (2) are enantiomers, as are (3) and (4), but both (1) and (2) are diastereomers of both (3) and (4). In particular, (1) and (3) are the diastereomeric esters of l-menthol and a racemic amino acid.

The diastereomeric esters used in this invention are readily separable by chromatography on a broad diversity of chromatographic supports using a broad range of solvents as eluants. Column selectivity can be defined by the quantity, $$\alpha = \frac{(t_2 - t)}{(t_1 - t)} = \frac{k_2}{k_1}$$

where $t_2$ and $t_1$ are the retention times of the two diastereomers and t is the retention time of unretained components. This column selectivity, alpha, is a measure of the ease of separation of components on a particular support and with a particular solvent as eluant. Increasing values of alpha represent increasing ease of separation. Values of alpha greater than about 1.3 imply that the separation is quite facile; values of alpha from about 1.1 to about 1.3 imply that the separation is feasible although not necessarily facile. It has been observed that the particular diastereomers of the racemic amino acids used in this invention frequently have alpha values above about 1.3.

The diastereomers used in this invention are esters from racemic amino acids, especially alpha amino acids, and optically active 2-isopropyl-5-methylcyclohexanol. The latter alcohol exists as four geometric isomers, each of which consists of a pair of enantiomers, for a total of 8 stereoisomers. The geometric relation between the isopropyl and methyl groups, respectively, vis-a-vis the hydroxyl group may be trans, cis (menthol), cis trans (neomenthol), trans, trans (isomenthol), or cis, cis (neoisomenthol). Any enantiomer of the above geometric isomers may be used in this invention. Menthol is an especially desirable isomer because of its availability, and 1-menthol is particularly preferred for the same reason.

Among the amino acids which may be resolved by the process of this invention are the naturally occuring amino acids such as alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, and valine. Examples of other amino acids which may be employed in the invention described herein and which are cited solely for illustrative purposes and which is not to be construed as limiting in any way, include 3,4-dihydroxyphenylalanine, 4-hydroxyphenylglycine, 3,5-diiodothyronine, and m-tyrosine.

A solution of the diasteromeric esters is contacted with a chromatographic support. It has been found that a broad range of supports may be used in the practice of this invention. One group of preferred supports is represented by silica, alumina, and the zeolites. Another group of supports which may be used in the practice of this invention consists of supports commonly used for reverse phase chromatography. Reverse phase chromatography is that branch of chromatography where the mobile phase is more polar than the stationary phase, or support. Among the supports which are used in reverse phase chromatography are modified silicas, i.e., silicas modified by silanization so as to bear nonpolar groups on the surface of the silica as replacements for surface hydroxyl groups. For example, such silicas may bear long-chain alkyl, aryl, amino, or cyano groups bonded to the surface via a silicon-bearing moiety.

The chromatographic support is eluted with a solvent or solvent system under chromatographic conditions. By "chromatographic conditions" is meant the general principles of separation by chromatography known to those skilled in the art and routinely applied to a liquid-solid chromatographic operation. Thus, for example, solvent flow is uniform, formation of gas bubbles is avoided, disturbance of the solid support is minimized, and so forth. The solvents which may be used in the process of this invention are those typical of chromatographic processes. Among such solvents are aliphatic hydrocarbons such as pentane, hexane, heptane, octane, nonane, decane, cyclopentane, cyclohexane, diisobutylene, pentene, hexene, etc.; aromatic hydrocarbons such as benzene, toluene, the xylenes, ethylbenzene, diethylbenzene, methylethylbenzene and the like; halogenated hydrocarbons, especially chlorinated and fluorinated hydrocarbons illustrated by chloroform, methylene chloride, carbon tetrachloride, chloropropane, chlorobutane, chloropentane, fluoralkanes, bromoethane, chlorobenzene, chlorotoluene, and ethylene chloride; sulfides, especially carbon disulfide; ethers as illustrated by diethyl ether, tetrahydrofuran, tetrahydropyran, and dioxane; esters, especially acetates, such as methyl acetate, butyl acetate, and esters of saturated carboxylic acids up to about 6 carbon atoms where the portion arising from the alcohol is saturated and contains up to about 6 carbon atoms; ketones containing up to about 8 carbon atoms, such as acetone, butanone, pentanone, hexanone, heptanone, and octanone; nitroalkanes such as nitromethane, nitroethane, nitropropane, and nitrobutane; amines, especially pyridine; nitriles, such as acetonitrile, propionitrile, and butyronitrile; alcohols containing up to about 8 carbon atoms, including diols and triols; acetic acid and dimethylsulfoxide.

At least one effluent fraction is collected containing a purified diastereomer. Often the effluent is monitored for a particular property to determine suitable effluent fractions. For example, it may be monitored for a particular ultraviolet or infrared absorbance or for its refractive index, as representative of properties often used to determine effluent fractions. Because the concentration of purified diastereomer may be low, differential measurements are especially valuable in determining effluent fractions.

After the effluent fraction or fractions containing a purified diastereomer is/are collected, the purified diastereomer is treated to liberate the optically active amino acid. The most common method of treating the purified diastereomer to afford optically active amino acid is hydrolysis. Quite typically hydrolysis is both acid and base catalyzed. Base catalyzed hydrolysis is somewhat preferred to maximize optical purity of the amino acid regenerated thereby, and also to minimize racemization of the liberated cyclohexanol which is recovered concurrently. Mineral acids exemplify suitable acid catalysts; alkali metal hydroxides and carbonates exemplify suitable base catalysts. The optically active amino acid is then recovered by suitable means.

The following examples merely illustrate this invention and are not intended to limit this invention in any way.

The chromatographic system employed in these examples was composed of a pump capable of flow rates up to 10 ml per minute at 10,000 psi, a septumless injector equipped with zero dead volume fittings, the appropriate column for separation, a dual-channel absorbance detector equipped for monitoring effluent at 254 and 280 nm, and a dual-channel recorder. All tubing used was stainless steel of 1/16" outside diameter with 0.009" inside diameter. The columns were of stainless steel, 4.6 mm inside diameter and 25 cm long.

All solvents used as eluants were degassed and filtered before use. The hexane was freshly distilled and the forward phase eluants were dried using anhydrous magnesium sulfate. All eluants and other chemicals described were obtained from commercial sources and used without further purification.

EXAMPLE 1

To a single neck 200 ml round bottom flask equipped with a Dean-Stark trap under a reflux condenser, a magnetic stirrer and a heating mantle was added 2.50 g (0.0165 moles) of d,l-phenylglycine, 3.00 g (0.0192 mole) of 1-menthol, 3.65 g (0.0192 mole) of para-toluenesulfonic acid monohydrate, 30 ml benzene and 13 ml toluene. The slurry was heated at a gentle reflux with stirring for 3 days while water was removed by azeotropic distillation. The cooled slurry was filtered, the solid was treated with 10% aqueous sodium carbonate, and the resulting base mixture extracted with diethylether. The ether phase was dried (magnesium sulfate) and solvent was removed to afford 4.3 g of a crystalline mixture of the diastereomers plus unreacted menthol which was subsequently removed by sublimation. One of the diastereomers was separately prepared from 1-menthol and 1-phenylglycine in a like manner.

EXAMPLE 2

The diastereomeic esters from racemic menthol and (−)-phenylglycine were prepared as described in Example 1. Separation was achieved on a silica gel column using a 2-propanol-hexane solvent system as eluant. The insensivity of the separation to eluant composition is shown in the following table which gives the alpha values measured for various eluants.

| Alpha Values for 2-Propanol-Hexane Mixtures on Silica Gel | |
|---|---|
| Eluant, % 2-propanol | α |
| 20 | 1.53 |
| 10 | 1.54 |
| 5 | 1.51 |
| 1 | 1.44 |

Since the diastereomeric pair used in these experiments is functionally equivalent to the diastereomeric pair from racemic phenylglycine and a menthol enantiomer, these experiments show the relative insensitivity of the diastereomeric esters of this invention to changes in eluants.

EXAMPLE 3

A solution containing 2.8 g of a diastereomeric mixture prepared according to Example 1 was chromatographed on 375 g silica gel using 20% 2-propanol-hexane as the eluant at a flow rate of 150 ml per minute. The diastereomers were recycled twice and four fractions were collected. The fractions containing the lesser retained diastereomer were combined to yield 0.90 g of material in 99% purity. The remaining fractions were combined to yield 1.1 g of the more retained diastereomer in 99% purity. The remainder of the material was composed mostly of 1-menthol.

EXAMPLE 4

The diastereomeric esters from racemic phenylglycine and 1-menthol as described in Example 1 were separated under reverse phase chromatographic conditions using an octadecylsilane-modified silica gel, the eluant being a solution composed of 10% 0.1 M ammonium acetate in water and 90% acetonitrile. The alpha value under these conditions was 1.08.

EXAMPLE 5

Diastereomeric esters of menthol with different amino acids were prepared by the general method of Example 1 from 1-menthol and racemic amino acids. Separation of each of the diastereomers was achieved on a silica gel column using 20% 2-propanol-hexane as the eluant. The accompanying table shows that the class of diastereomeric esters of menthol and an amino acid has alpha values leading to feasible chromatographic separation, with many members having an α-value making such separation quite facile.

| Alpha Values of Diastereomeric Esters of 1-Menthol on Silica Gel Using 20% 2-Propanol-Hexane as Eluant | |
|---|---|
| Amino acid | α |
| phenylglycine | 1.53 |
| 4-hydroxyphenylglycine | 1.39 |
| tyrosine | 1.10 |
| phenylalanine | 1.14 |
| tryptophan | 1.30 |

EXAMPLE 6

To 0.92 g (0.00303 moles) of 1-phenylalanine-1-menthylester in a 100 ml round bottom flask equipped with a magnetic stirrer was added 2.5 equivalents of sodium hydroxide dissolved in 9 ml of methanol. After 5 hours at room temperature, 15 ml of water was added to the reaction mixture and the resulting solution was extracted three times with about 20 ml portions of diethylether. The ether extract was dried with anhydrous magnesium sulfate, filtered, and concentrated to yield 0.39 g of 1-menthol. The aqueous phase was neutralized with dilute hydrochloric acid then treated with 2-propanol and the water and methanol removed azeotropically to yield a residue of sodium chloride and phenylalanine. The residue was carefully extracted with just enough water to remove the sodium chloride while leaving the phenylalanine. The phenylalanine residue was dried using azeotropic extraction with 2-propanol, then vacuum dried to yield 0.36 g of white powder, $[\alpha]_D^{20} = -33.3 \pm 1.6°$ (c 1.23, H$_2$O).

What is claimed is:

1. A method of preparing optically active amino acids comprising contacting a solution containing the diastereomeric esters from a racemic amino acid and an optically active 2-isopropyl-5-methylcyclohexanol with a chromatographic support selected from the group consisting of silica, alumina, modified silicas, and the zeolites, eluting said support with a solvent under chromatographic conditions, collecting at least one effluent fraction containing a purified diastereomer, hydrolyzing the purified diastereomer to liberate an optically active amino acid, and recovering said optically active amino acid.

2. The method of claim 1 wherein the cyclohexanol is menthol.

3. The method of claim 2 where the menthol is 1-menthol.

4. The method of claim 1 where the optically active amino acid is L-3,4-dihydroxyphenylalanine.

5. The method of claim 1 where said hydrolysis is base catalyzed.

6. The method of claim 1 where said hydrolysis is acid catalyzed.

* * * * *